United States Patent [19]

Shimamura et al.

[11] Patent Number: 4,737,153
[45] Date of Patent: Apr. 12, 1988

[54] REINFORCED THERAPEUTIC TUBE

[75] Inventors: Hidehiko Shimamura; Yoshihiko Yamada, both of Ogaki; Hiroyuki Akasu; Akio Ohmory, both of Kurashiki; Toshiaki Takagi, Nishinomiya, all of Japan

[73] Assignee: Kuraray Co., Ltd., Kurashiki, Japan

[21] Appl. No.: 10,965

[22] Filed: Feb. 4, 1987

[30] Foreign Application Priority Data

Feb. 7, 1986 [JP] Japan .............................. 61-17027[U]
Aug. 29, 1986 [JP] Japan ............................ 61-133075[U]

[51] Int. Cl.[4] .......................................... A61M 25/00
[52] U.S. Cl. .................................. 604/282; 128/658; 138/174
[58] Field of Search .............................. 604/282, 280; 128/656–658; 138/174, 132, 133, 146

[56] References Cited

U.S. PATENT DOCUMENTS 2,211,975  8/1940  Hendrickson ...................... 604/282
3,426,744  2/1969  Ball .................................. 604/282 X

FOREIGN PATENT DOCUMENTS 0102422  3/1984  European Pat. Off. .

*Primary Examiner*—Stephen C. Pellegrino
*Attorney, Agent, or Firm*—Oblon, Fisher, Spivak, McClelland & Maier

[57] ABSTRACT

A reinforced therapeutic tube which is excellent in kink resistance, pressure resistance and flexibility. The tube is made of an elastomeric material with a reinforcing material spirally embedded into the tube wall, and at least one of the tubular parts where no spiral reinforcing material exists. The tip end of the reinforcing material which is wound in spiral shape is bent parallel to the inside surface of the tube and inward of the tube for at least one or more pitches of the spiral, and at least the tip of the reinforcing material bent is buried into the inside wall of the tube.

21 Claims, 4 Drawing Sheets

REINFORCED THERAPEUTIC TUBE

BACKGROUND OF THE INVENTION

1. Field of the Invention:

The present invention relates to reinforced therapeutic tubes of various types for use in the fields of anesthesia and respiratory control, etc., such as catheters, oral and nasal endotracheal tubes, tracheal cannulae, etc., and particularly pertains to reinforced therapeutic tubes with a spiral shape reinforcing material embedded into the wall of the tube body, which are excellent in kink resistance, pressure resistance and flexibility.

2. Description of the Prior Art:

Heretofore, for therapeutic tubes for bringing fluids into and out of living body, various types have been proposed. The simplest one of them all is catheter. For therapeutic tubes having more complex structures than catheters, there are available endotracheal tubes, tracheal cannulae and various tubes for drainage, etc.

Such therapeutic tubes are required to have flexibility and thin wall. However, to make the flow rate of fluid adequate by making the wall thin is quite opposite to make the tube difficult to collapse. The thinner the tube wall, the larger the hazard of the tube collapsing. Should a tube collapse and be blockaded, while in use, it would bring serious trouble or even death to the patient who is using it. For this reason, such a therapeutic tube must be of a structure which would not be blockaded, even if bent with a small radius.

Recently, proposals have been made to spirally embedded into the tube wall a reinforcing material such as stainless steel wire or piano wire, etc., being in wire form or one in thin plate form with narrow width, to provide such a therapeutic tube with resistance to blockading (Japanese Patent Application Laid-Open No. 38565/1983, etc.) Such a therapeutic tube having a spiral shape reinforcing material inside the tube wall is called "reinforced tube".

However, a tube having such a reinforcing material embedded into the tube wall in spiral form tended to expand its ID at both ends of the tube body owing to the resilience of the spiral shape reinforcing material under external force; accordingly, when the tube wall was thin, the tip of the reinforcing wire broke through and projected out of the tube wall, thereby injuring the tracheal inner wall. As a method for preventing this, it has been proposed to fix by welding the tip of the spiral wire onto a neighboring spiral wire turn, but because the wire is fine, the welding is technically difficult; even if the welding has been successfully made, strain will develop in the weld, moreover, the welded part will thickly swell up, possibly causing breakage of thin tube wall.

As an example of solving the above mentioned problem, a flat wire is spirally embedded in the tube wall. This makes for easy welding of wire, but the welded part swells up, and because of the wire being flat, flexibility is poor, thus posing problems.

SUMMARY OF THE INVENTION

An object of this invention is to provide smooth surfaced thin reinforced therapeutic tube., which is safe, with no strain arising near the tube end parts, thus no reinforcing material tip projecting out of the tube wall, by positively preventing the recoiling of the tip of the spiral shape reinforcing material, which occurs when external force is imposed on the tube or in the like events.

Another object of this invention is to provide reinforced therapeutic tube excellent in kink resistance, pressure resistance and flexibility.

Still another object of this invention is to provide reinforced therapeutic tubes excellent in blockading resistance, such that it will not be blockaded, even if bent with small radii.

These objects may be achieved by providing a reinforced therapeutic tube axially integrally formed of a tube body with a reinforcing material spirally embedded into the tube wall and at least one of tubular parts where no spiral reinforcing material exists, in which at least one end of the spiral shape reinforcing material is bent inward of the tube to a length such that it is engaged onto at least a neighboring spiral turn, and moreover, at least its tip of the reinforcing material bent is buried in the tube wall.

Figure 1:
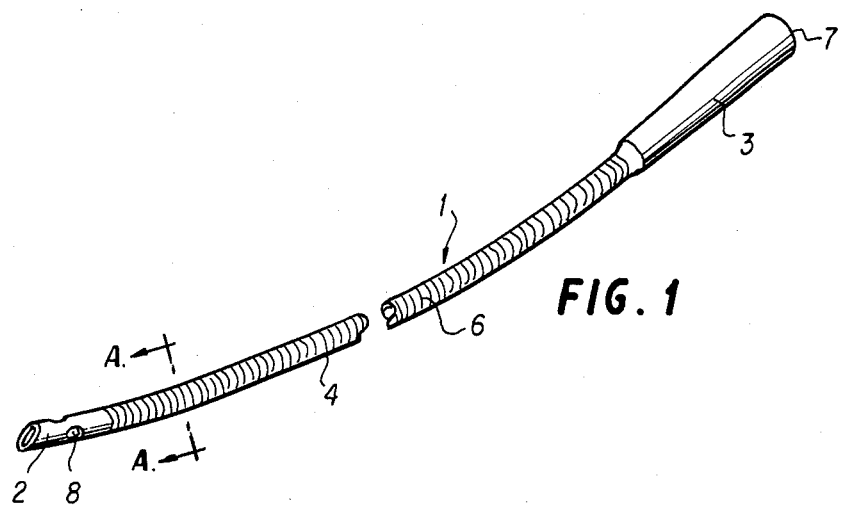
FIG. 1 is a perspective view of an example of the reinforced therapeutic tube of this invention.

1 ... Catheter 2 ... Tubular part 3 ... Accepter 4 ... Tube body 5 ... Hollow 6 ... Reinforcing material 7 ... Proximal end 8 ... Side hole 9 ... Tip end of reinforcing material 10 ... Portion of the tubular part in contact with tube body 11 ... Hollow 12 ... Endotracheal tube 13 ... Cuff 14 ... Pilot tube 15 ... Pilot balloon 16 ... Luer connector

DETAILED DESCRIPTION OF THE INVENTION

The materials for use in therapeutic tube of this invention, there may be mentioned polyvinyl chloride, polyurethane, polyurethane urea, silicone rubber, fluororubber or other materials having equivalent initial tensile modulus to theirs. Of these materials, segmented polyurethane consisting of soft segment and hard segment has high biocompatibility, and excells in the elastic recovery percentage of elongation; therefore, it is preferable as an elastomer for thin, small bore catheter.

In the reinforced therapeutic tube of this invention, the tube body with a reinforcing material spirally embedded into the tube wall and at least one of tubular parts where no spiral reinforcing material exists are integrally formed in its axial direction. In this embodiment, the tube is composed so as to have flexibility.

The tubular parts may be integrally formed at both ends of the tube body, one of which may be an accepter.

In the reinforced therapeutic tube of this invention, the tip end of the reinforcing material which is wound in spiral shape is bent parallel to the inside surface of the tube and inward of the tube for a length of at least one or more pitches of the spiral, preferably 1–30 mm, more preferably 2–10 mm, and moreover, at least the tip of the reinforcing material bent is buried into the inside wall of the tube.

According to this invention, the possibility of the tip of the reinforcing material breaking through the tube wall is readily and positively preventable by such a device as hereabove described. If the tube-inward bending back of the spiral end were short, and it were not engaged onto the neighboring turn of the spiral, however, the spiral tip sometimes might break through the tube wall; it is for this reason necessary that the end of the spiral should be bent back to a length longer than at least one neighboring pitch of the spiral, and the end of the reinforcing material securely engaged onto the neighboring turn of the spiral. According to this invention, since as described hereabove, the spiral end bent inward of the tube is always engaged onto the neighboring turn of the spiral because of the tendency of the spiral to expand its diameter; therefore, the spiral tip will never break through said tube wall.

As reinforcing materials for use in therapeutic tubes of this invention, there may be mentioned metal wires normally having initial tensile resistivity higher than $1 \times 10^4$ kg-f/mm$^2$, such as steel wire, stainless steel wire, tungsten wire, etc., various synthetic fibers such as polyvinylalochol fibers, acrylic fibers, polysulfone, vinylidene, polyurethane, polyethylene, polypropylene, nylon, aromatic polyamide (aramid), polyesters such as polyethylene terephthalate, polybutylene terephthalate, aromatic polyesters (arylate), etc., and besides, protein fibers and carbon fibers, etc. Of these reinforcing materials, tungsten wire, having a high initial tensile resistivity, is preferably used.

Figure 2:
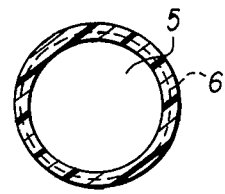
FIG. 2 is a view of A—A section of FIG. 1.
Figure 3:
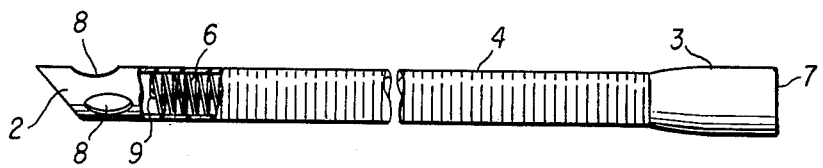
FIG. 3 is a side view of the tube of FIG. 1.

In the following, preferred embodiments of the reinforced therapeutic tube of this invention are described with reference to the accompanying drawings, but this invention will not be limited to these embodiments only. FIG. 1 is a perspective view showing a blood removing and sending catheter for extracorporeal circulation of blood in cardiotomy, lung assist, etc.; FIG. 2, a view of A—A section of FIG. 1; and FIG. 3, a side view of said catheter.

Said catheter 1 is composed of tubular part 2, accepter 3 and tube body 4 which connects them. The catheter has a hollow 5 formed through the whole length thereof. Along the tube body 4 of the catheter, a spiral shape reinforcing material 6 is embedded in its wall, but no reinforcing material exists in the tubular part 2 and the accepter 3. In this embodiment, the catheter 1 is so composed as to have flexibility, using polyvinyl chloride, polyurethane, polyurethane urea, silicone rubber, fluororubber or other materials having equivalent initial tensile resistivity to theirs. Of these materials, segmented polyurethane consisting of soft segment and hard segment has high biocompatibility, and excells in the modulus of elongation elasticity; therefore, it is preferable as an elastomer for thin, small bore catheter. Along the tube body 4 of the catheter 1, a spiral shape reinforcing material 6 is embedded in the tube wall. This spiral shape reinforcing material 6 is made of a wire with a diameter 0.02–1.0 mm, preferably, 0.05–0.4 mm, and with a pitch 0.1–4 mm.

Lest the tip of the spiral shape reinforcing material 6 should break through the tube wall, before joining the tubular part 2 to the tube body, the tip end 9 of the reinforcing material 6 is bent back inward of the tube to a length such that it is engaged onto at least a neighboring spiral turn, as shown in FIG. 3, 5, 10 and 11. At least the tip 9 of said bent back reinforcing material 6 is buried in the tube inner wall, to be directly in contact with the neighboring spiral turn owing to its repelling force. If the elasticity of the tube is large, the end of the reinforcing material is in contact with the neighboring spiral turn through the compressed thin tube inner wall.

At least the tip end 9 of the reinforcing material 6 may be completely buried into the tube wall by coating the inside surface of the tube with an elastomer solution. This sometimes produce some swell on the tube inside surface, but this swell is in a gentle hill shape, posing no practical problem at all. The accepter 3 of the catheter 1 is provided with a joint (not shown in drawings). Since normally, the ID of the proximal end 7 of the accepter 3 is made larger than the ID of the tube body 4, the wall surface of accepter 3 of catheter 1 is slightly expanded, as the end of the joint is inserted, whereby the joint is secured on the catheter 1.

Figure 6:
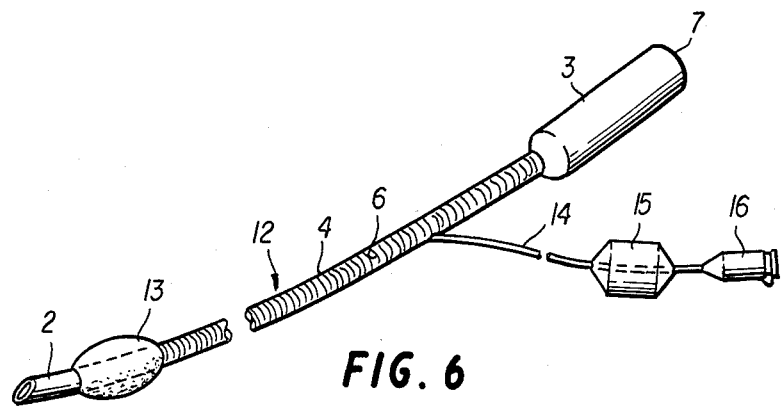
FIG. 6 is a perspective view of an endotracheal tube, being one of reinforced therapeutic tube of this invention.

FIG. 6 is a perspective view of an endotracheal tube, being an embodiment of the reinforced therapeutic tube of this invention, showing that the ID of the accepter 3 is equal to the ID of the tube body 4, or is somewhat enlarged therefrom toward its proximal end 7. Irregularities on the inside surface of said accepter, if any, would undesirably give rise to pooling of secretions, when sucking them and so on; for this reason, the connection of the accepter to the tube body should desirably be finished as smooth as possible.

Figure 7:
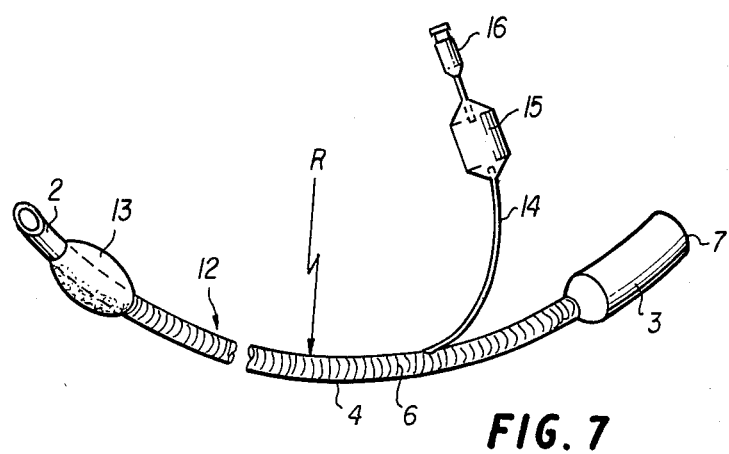
FIG. 7 is a perspective view of an endotracheal tube bent in a shape of a waxing moon at a radius of curve (R) with its forward end placed on the left side, being an example of reinforced therapeutic tube of this invention.

FIG. 7 is an endotracheal tube bent at a radius of curve (R) of 100–180 mm, illustrating an endotracheal tube with its opening positioned on the upper surface side, when it is placed in a shape of a waxing moon with its tip end on the the left.

The tubular part 2 of the catheter 1 or the endotracheal tube 12 shall be connected with the tube body 4 of the catheter smoothly both on the in- and out-side surfaces, to be integrated therewith, and shall have no reinforcing material therein. This tubular part 2 should desirably be properly rounded at the end opening so as not to injure the living body, when the catheter is inserted thereinto. And for prevention of blockading of the tip end opening, more than one side hole 8 may be provided through the wall surface of the tip end.

Such catheters 1 may be formed with various sizes. Normally, many of them have overall lengths of 5–100 cm, preferably 10–45 cm; ID 0.2–20 mm, preferably 2–12 mm; and wall thicknesses 0.2–1.5 mm.

Figure 8:
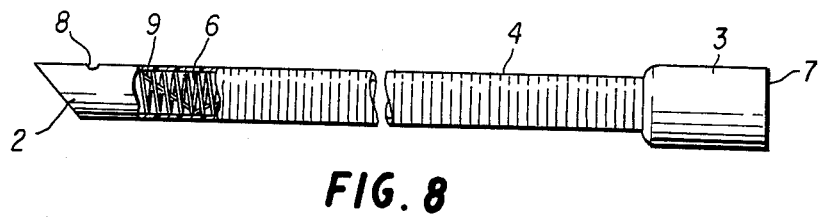
FIG. 8 is a side view of another endotracheal tube of this invention.

Endotracheal tubes should have overall lengths of 5–50 cm, preferably 15–35 cm; ID 0.2–20 mm, preferably 2–8 mm; wall thicknesses 0.15–1.5 mm, lengths of the tubular part 2 1–20 mm, preferably 2–10 mm; and lengths of accepter 3 10–50 mm, preferably 15–25 mm. And as desired, a so-called cuff 13 as a means for securing hermetic sealing between the tube and the tracheal may be provided at a distance of 5 mm, preferably 10 mm or longer, from the tip. It is no matter whether any side hole is provided or not, but for an endotracheal tube of which tubular part end is beveled, as shown in FIG. 6 and 8, it is desirable to provide a side hole of a size smaller than 80% of the tubular part ID on the opposite side to the bevel.

The therapeutic tube of this invention may be manufactured in the following manner: First, a thin wall core-tube is made by extruding or by coating a solution of elastomer on a mandrel, followed by drying; Next, the reinforcing material is wound in spiral shape by a fixed pitch on the core-tube thus obtained. After that, an elastomer of the same quality with the core-tube or an elastomer of the different quality from the core-tube, extruded by use of an extruder, or a solution of elastomer is coated on the surface of the core-tube thus obtained. The tube obtained after drying is cut to a length such that it will have the intended length, when the tubular part 2 and the accepter 3, having no spiral shape reinforcing material, are integrally formed. Then, at least one end of the reinforcing material of the tube thus cut is drawn out from the elastomer part, or taken out by cutting off the elastomer; the end of the reinforcing material is bent inward of the tube by means of a pincette etc., and thereafter, a solution of elastomer is coated on the reinforcing material part bent inward of the tube, followed by drying. In that way, the tube body 4 is formed.

Figure 4:
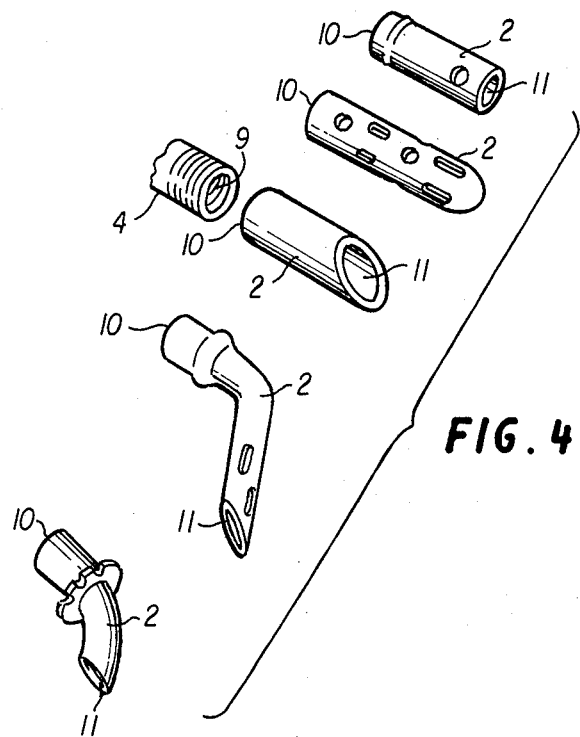
FIG. 4 is a perspective view showing examples of the tubular part for being joined to the tube body.
Figure 5:
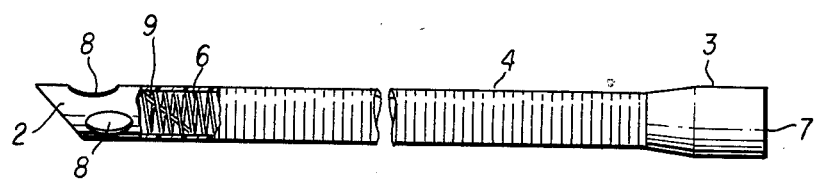
FIG. 5 is a side view showing another mode of the reinforced therapeutic tube of this invention.
Figure 9:
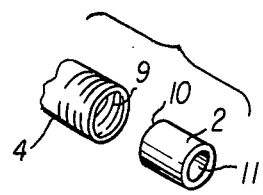
FIG. 9 is a perspective view showing an example of the tubular part which is used in manufacturing the therapeutic tube of this invention.
Figure 10:
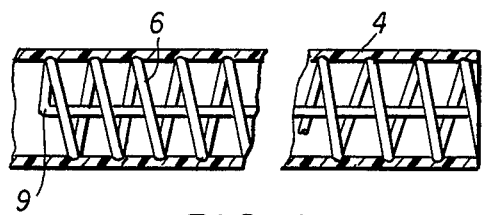
FIGS. 10 and 11 are side views showing other modes of the therapeutic tube of this invention; in the former, the forward end of the reinforcing material is brought back to the other end, and in the latter, it is wound back at a pitch larger than that of the outside spiral.
Figure 11:
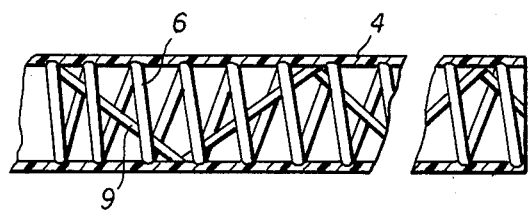

The tubular parts in which no reinforcing material is contained are normally formed separately from the tube body 4 as a tubular single unit having a hollow portion 11 therein by making use of a well-known forming technique such as injection molding etc., as shown in FIG. 4 and 9, after which it is bonded or fused to the tube body by any well-known method. For example, metal powder is contained in the portion 10 of the tubular part 2 which is to be brought in contact with the tube body 4, so that the portion containing the metal powder is to be molten by induction heating, causing the tubular part 2 to be joined with the tube body 4. The tubular part 2 is formed of the same material as the tube body 4, or when it needs to be formed of a material softer or harder than the tube body 4, different materials may be used.

By the method hereabove mentioned, the external surface of the connection between the tube body 4 and the tubular part 2 may be formed in smooth state. To make the external surface of the connection smooth is important to facilitate insertion and removal of the catheter into and out of the living body. Further, by coating an elastomer solution on the internal surface of the connection between the tube body 4 and the tubular part 2, it is possible to make the internal surface side of the connection smooth. Then by bringing the internal surface of the connection into a smooth state, thrombosis, settling and pooling of secretions and contaminants, and settling of body fluids may be prevented.

The accepter 3 is connected to the tube body 4 by the similar method as the tubular part 2. At this instance also, the end of the spiral shape reinforcing material on the accepter side of the tube body should desirably be bent inward of the tube to a length such that it is engaged onto a neighboring spiral turn, and moreover, at least the bent tip is buried into the tube wall, or buried into the accepter side. If the wall of the accepter is so thick that the tip of the reinforcing material may not break through the wall, such treatment may be dispensed with.

What is claimed is:

1. A reinforced therapeutic tube axially integrally formed of a tube body with a reinforcing material spirally embedded into the tube wall and at least one of tubular parts where no spiral reinforcing material exists, characterized in that at least one end of the spiral shape reinforcing material is bent inward of the tube to a length such that it is engaged onto at least a neighboring spiral turn, and moreover, at least its bent tip is buried in the tube wall.

2. The reinforced therapeutic tube of claim 1 wherein the tubular parts are axially integrally formed at both ends of the tube body.

3. The reinforced therapeutic tube of claim 2 wherein one of the tubular parts is an accepter.

4. The reinforced therapeutic tube of claim 1 wherein the tube body is composed of segmented polyurethane.

5. The reinforced therapeutic tube of claim 1 wherein the tube body is composed of polyvinyl chloride.

6. The reinforced therapeutic tube of claim 1 wherein the reinforced material has initial tensile resistivity higher than $1 \times 10^4$ kg-f/mm$^2$.

7. The reinforced therapeutic tube of claim 1 wherein the reinforcing material is tungsten wire.

8. The reinforced therapeutic tube of claim 1 wherein the length of reinforcing material bent back inward of the tube is 1–30 mm.

9. The reinforced therapeutic tube of claim 1 wherein the reinforcing material is wound in spiral shape on the core-tube by a pitch of 0.1–4 mm.

10. The reinforced therapeutic tube of claim 1 wherein the tube is a tube for catheter.

11. The reinfoced therapeutic tube of claim 10 wherein the overall length of tube is 5–100 cm.

12. The reinforced therapeutic tube of claim 10 wherein the overall length of tube is 10–45 cm.

13. The reinforced therapeutic tube of claim 10 wherein the ID of the tube is 0.2–20 mm.

14. The reinfoecde therapeutic tube of claim 10 wherein the ID of the tube is 2–12 mm.

15. The reinforced therapeutic tube of claim 10 wherein the wall thickness is 0.2–1.5 mm.

16. The reinforced therapeutic tube of claim 1 wherein the tube is a tube for endotracheal tube.

17. The reinforced therapeutic tube of claim 16 wherein the overall length of the tube is 5–50 cm.

18. The reinforced therapeutic tube of claim 16 wherein the overall length of the tube is 15–35 cm.

19. The reinforced therapeutic tube of claim 16 wherein the ID is 0.2–20 mm.

20. The reinforced therapeutic tube of claim 16 wherein the ID of the tube is 2–8 mm.

21. The reinforced therapeutic tube of claim 16 wherein the wall thickness is 0.15–1.5 mm.

* * * * *